(12) United States Patent
Stoll et al.

(10) Patent No.: US 6,978,173 B2
(45) Date of Patent: Dec. 20, 2005

(54) DEVICE FOR INFLUENCING CELL-GROWTH MECHANISMS IN VESSELS OF A HUMAN OR ANIMAL BODY

(75) Inventors: Hans-Peter Stoll, St. Ingbert (DE); Robert Schmiedl, Erlangen (DE)

(73) Assignee: Biotronik Mess- und Therapiegeraete GmbH & Co., (DE)

( * ) Notice: Subject to any disclaimer, the term of this patent is extended or adjusted under 35 U.S.C. 154(b) by 429 days.

(21) Appl. No.: 10/002,643

(22) Filed: Oct. 31, 2001

(65) Prior Publication Data

US 2002/0138100 A1     Sep. 26, 2002

(30) Foreign Application Priority Data

Nov. 3, 2000    (DE) ................. 100 55 686

(51) Int. Cl.[7] .............................................. A61N 1/00
(52) U.S. Cl. ...................... 607/2; 607/50; 623/1.15
(58) Field of Search ................. 600/9–15; 607/2, 607/50–51; 623/1.1–1.22

(56) References Cited

U.S. PATENT DOCUMENTS

| | | | |
|---|---|---|---|
| 3,890,953 A * | 6/1975 | Kraus et al. ................. 600/14 |
| 3,915,151 A * | 10/1975 | Kraus ......................... 600/13 |
| 4,266,532 A * | 5/1981 | Ryaby et al. ................ 600/14 |
| 4,359,453 A * | 11/1982 | Gordon ....................... 424/1.37 |
| 4,665,898 A * | 5/1987 | Costa et al. ................. 600/14 |
| 4,674,482 A * | 6/1987 | Waltonen et al. ........... 600/14 |
| 5,078,736 A | 1/1992 | Behl |
| 5,105,017 A * | 4/1992 | Dillard ........................ 568/64 |
| 5,211,622 A * | 5/1993 | Liboff et al. ................ 600/9 |
| 5,476,438 A | 12/1995 | Edrich |
| 5,718,246 A * | 2/1998 | Vona .......................... 128/898 |
| 6,030,334 A * | 2/2000 | Cox et al. .................... 600/12 |
| 6,280,385 B1 | 8/2001 | Melzer |
| 6,561,968 B1 * | 5/2003 | Dissing et al. .............. 600/13 |
| 6,650,943 B1 * | 11/2003 | Whitehurst et al. ......... 607/39 |

FOREIGN PATENT DOCUMENTS

| | | |
|---|---|---|
| DE | 2 315 517 | 10/1973 |
| DE | 26 36 818 C2 | 2/1978 |
| DE | 30 46 764 A1 | 9/1982 |
| DE | 32 31 837 A1 | 3/1984 |
| DE | 39 30 930 C1 | 10/1990 |
| DE | 43 09 395 A1 | 9/1993 |
| DE | 44 08 110 A1 | 9/1994 |
| DE | 197 46 735 A1 | 4/1999 |

(Continued)

OTHER PUBLICATIONS

Indolfi, et al., "Mechanisms of restenosis afetr angioplasty and approach to therapy," Intl J. of Molecular Med., p. 143-48, ( May 28, 1998).

(Continued)

*Primary Examiner*—Mark Bockelman
(74) *Attorney, Agent, or Firm*—Hahn Loeser & Parks, LLP; John J. Cunniff

(57) ABSTRACT

A device for influencing cell-growth mechanisms in vessels, in particular blood vessels, of a human or animal body, wherein to influence the cell growth mechanisms there is provided an excitation device (5; 5"') which is adapted to produce stimulation currents in a region to be treated of the vessel (3; 3"'), wherein the frequency and/or the modulation frequency of the stimulation currents is in the range of frequencies at which distribution of secondary messenger substances controlling cell growth in the cells of the vessel (3; 3"') is influenced. Implant for influencing cell-growth mechanisms in such vessels.

22 Claims, 7 Drawing Sheets

FOREIGN PATENT DOCUMENTS

| | | |
|---|---|---|
| DE | 198 19 634 A1 | 11/1999 |
| DE | 198 24 504 A1 | 12/1999 |
| EP | 1 036 574 A1 | 9/2000 |
| WO | WO 00/13585 A1 | 3/2000 |

OTHER PUBLICATIONS

Nindl, et al., "Experiments showing that electromagnetic fields can be used to treat inflammatory diseases," Biomedical Sciences Instrumentation, p. 7-13, (Apr. 28, 2000).

Betz, E., "Migration and Proliferation of Vascular Smooth Muscle Cells," Drug Research, vol. 40 (No. 3a), p. 362-65, (May 28, 1990).

Herman Dertinger, "Hochwirksame Elektotherapie gegen Schuppenflechte," Spektrum der Wissenschaft, p. 15-17, (Apr. 29, 2000).

Charles Polk, "Electrical and Magnetic Fields for Bone and Soft Tissue Repair," Handbook of Biological Effects of Electromagnetic Fields, 2nd ed., CRC Press (United States of America), p. 231-46, (Oct. 29, 1996).

* cited by examiner

DEVICE FOR INFLUENCING CELL-GROWTH MECHANISMS IN VESSELS OF A HUMAN OR ANIMAL BODY

The present invention concerns a device for influencing cell-growth mechanisms in vessels, in particular blood vessels, of a human or animal body. It further concerns an implant for insertion into a vessel of a human or animal body, in particular a stent.

BACKGROUND OF THE ART

Cell-growth mechanisms in the vessel wall regularly play an important part in connection with the treatment of defects of vessels in the human or animal body. Cell growth can be on the one hand a cause of such a defect, as is the case for example with stenoses in blood vessels. Reduced or slow cell growth however can also be for example the cause of unsatisfactorily slow healing of defects in a vessel.

A number of widely different illnesses can result in so-called stenoses, that is to say constrictions in vessels in the body, with in part serious or even fatal consequences. Blood vessels are often affected in that respect. Thus for example arteriosclerosis with the vessel constrictions that it entails represents the most important and most frequent morbid change in the arteries, which can involve very serious consequences.

Various procedures have been adopted for the treatment or prophylaxis of such stenoses. Thus for example for stenosis prophylaxis or for the treatment of constrictions which have not yet progressed very far, medication treatments are used and the patient is prescribed an appropriate diet, while more advanced stenoses are generally treated by operative intervention. In that situation the affected locations in the vessel are mostly expanded by means of a balloon catheter. In that balloon dilation procedure, it is frequently necessary to insert a so-called stent into the vessel in order to hold it in an expanded condition.

In order to prevent so-called re-stenoses after the vessel has been treated, besides medication treatments and suitable adjustment to the nutrition of the patient, stents have also been proposed, which on their side towards the vessel are covered with cloths or the like in order to prevent renewed constriction of the vessel as a result of the vessel wall growing into the passage of the vessel, which is caused by cell growth, that is to say uncontrolled proliferation of the cell wall vessels. The proposed methods suffer from various disadvantages. Thus, adjustment to diet can often only have a supporting effect while medicational treatment can admittedly mostly be used with really good success, but it can give rise to widely varying side-effects according to the respective patient. Invasive treatment with a stent of a suitable configuration, which completely covers the wall of the vessel, is on the one hand relatively complicated and expensive, while on the other hand it is not possible to foresee to what extent unretarded cell proliferation or growth under the covering becomes a possibly menacing strain for the vessel.

In general terms, only medicational treatments with the disadvantages already referred to above are proposed for the purposes of speeding up healing of defects of a vessel, for example for accelerated healing of the wound after a surgical intervention.

SUMMARY OF THE INVENTION

Therefore the object of the present invention is to provide a device for influencing cell-growth mechanisms in vessels, which suffers from the above-described disadvantages at least to a lesser degree and which in particular can be used with a lower degree of complication and as few side-effects for the patient as possible.

That object is attained by a device for influencing cell-growth mechanisms in vessels, in particular blood vessels, of a human or animal body, comprising an excitation device for producing stimulation energy, and an implant, wherein the implant is adapted to be placed in a blood vessel and is further adapted to contactlessly receive stimulation energy from the excitation device and produce stimulation currents in a region to be treated of the vessel, and wherein the stimulation currents have a frequency and/or a modulation frequency in the range of frequencies at which distribution of secondary messenger substances controlling cell growth in the cells of the vessel is influenced. In addition, that object is attained by an implant for insertion into a vessel, in particular a blood vessel, of a human or animal body, where the implant has an excitation device nearby, and where the implant comprises a tubular body for bearing against the wall of the vessel, and the tubular body comprises, in at least in a portion-wise manner, a soft-magnetic material for concentration of a magnetic field produced by the excitation device and, by an implant for insertion into a vessel, in particular a blood vessel, of a human or animal body, wherein the implant stimulates cells of the vessel by means of stimulation currents, such stimulation influencing cell-growth mechanisms.

The present invention involves the technical teaching that it is possible to achieve an advantageous influence on cell-growth mechanisms in the vessel wall by means of a suitable device for the electrostimulation of the cells of the vessel wall with stimulation currents at low cost and complication and with slight side-effects from the point of view of the patient. In that respect, depending on the respective situation of use, it is possible to achieve at least partial suppression of cell-growth mechanisms, as is required for example to prevent or slow down stenoses. Equally however it is also possible to provide for stimulation of cell growth or cell proliferation, as is advantageous for example to speed up wound healing or to stabilise such vessels.

Hitherto electrostimulation for the purposes of suppressing cell-growth mechanisms has been known only in connection with the treatment of psoriasis for skin cells which naturally are at the surface of the body and are therefore readily accessible for simple stimulation with suitable stimulation currents by direct contacting (see Spektrum der Wissenschaft, Monatsspektrum, April 2000, pages 15 through 17, Spektrum der Wissenschaft Verlagsgesellschaft mbH, Heidelberg, Del.).

It has been found that the advantages of electrostimulation can also be achieved with simple means in the region of vessels, that is to say in the interior of the body which is not readily accessible, at a low level of complication and without side-effects from the point of view of the patient, if in accordance with the invention there is provided an excitation device for producing stimulation currents in a region of the vessel, which is to be treated. In that respect, in accordance with the invention, the excitation device is adapted to produce low-frequency stimulation currents whose frequency is in the range of frequencies at which the distribution of secondary messenger substances controlling cell growth, in particular cyclic adenosine monophosphate (cAMP) in the cells of the vessel is influenced, that is to say checked or stimulated. As in that respect the biologically effective information is in the frequency and/or modulation pattern of the stimulation currents, the same effect can be achieved if in accordance with the invention the excitation device is adapted to produce low-frequency modulated stimulation currents, in which case then the modulation frequency is in the range of frequencies at which the distribution of secondary messenger substances controlling cell growth, in particular cyclic adenosine monophosphate (cAMP) in the cells of the vessel is influenced, that is to say checked or stimulated. Equally suitably low-frequency stimulation currents can additionally also involve suitable low-frequency modulation. The frequency in question can differ from one cell type to another. In that respect for example a higher level of concentration of cyclic adenosine monophosphate reduces the division activity of the cells while that is increased by a reduced level of concentration.

Preferably the excitation device is adapted to produce stimulation currents whose frequency and/or modulation frequency is in the range of frequencies at which the distribution of secondary messenger substances controlling cell growth in the smooth muscle cells and additionally or alternatively in the endothelium cells and additionally or alternatively in the fibroblasts of the vessel is influenced as growths of those cell types play for example the major part in stenosis formation, in particular in blood vessels. Alternatively cell growth can also be stimulated by a suitable selection of the frequencies involved, for example in order to speed up healing of a wound. Equally it may be desirable to strengthen weakened vessel portions as for example frequently play a part in the formation of aneurysms, by virtue of increased cell growth in order to increase their capacity for resistance to the loadings acting on the wall of the vessel.

In that respect, the excitation device is preferably adapted to produce stimulation currents in the region of the vessel to be treated, at a frequency and/or modulation frequency of up to 200 Hz, preferably between 10 and 100 Hz, as it is in that range, in terms of distribution or inhibition of said secondary messenger substances, that there are 'resonance frequencies' in respect of the cells, at which it is possible to achieve particularly good results. The invention can be used to treat the most widely varying vessels in a human or animal body, but it can be used to particular advantage in connection with the treatment of blood vessels.

In preferred variants of the device according to the invention the excitation device has a time control device which is adapted for stepwise or continuous reduction in the level of stimulation intensity and additionally or alternatively is adapted for stepwise or continuous reduction in the frequency of stimulation. That makes it possible to achieve what is referred to as 'winding-down' of the treatment, in which the artificial suppression or stimulation of cell growth processes is stepwise or continuously reduced in order to prevent overshoot growth of the cells or complete suspension of cell growth in response to abrupt termination of the treatment.

Preferably the excitation device is adapted for contact-less production of the stimulation currents in the region of the vessel which is to be treated, as in that way precisely in a treatment extending over a relatively long period of time, it is possible to provide for particularly simple stimulation without the patient possibly having to be repeatedly subjected to surgical intervention. Equally however it is also possible for the excitation device to be arranged for example in a catheter or to be connected thereto, which is moved for the treatment to the location which is to be treated.

Advantageous configurations of the device according to the invention are distinguished in that the excitation device is adapted for direct induction of the stimulation currents in the body tissue of the vessel region which is to be treated. Preferably in that case the excitation device includes an induction device for producing at least one local magnetic alternating field in the treatment region of the vessel so that the stimulation currents of suitable frequency and/or modulation frequency and appropriate intensity are induced by the magnetic alternating field directly in the tissue to be treated. Preferably magnetic alternating fields of relatively high frequency are mutually superimposed in order to produce electrical alternating fields of slightly differing frequency, which are superimposed in the manner of a beat to form an electrical field involving low-frequency modulation. Equally however it is also already possible to produce a magnetic alternating field which correspondingly involves low-frequency modulation. In other words the beat or modulation can be produced both within and also outside the body.

The induction device may include any means for producing a magnetic alternating field. Thus for example it is possible to use flat coils or pairs of coils, for example a Helmholtz coil arrangement, or straight, preferably long coils, in the form of a an electromagnet, which depending on the position in respect of depth of the treatment region in the body are applied to the body of the patient or are positioned at a spacing therefrom. In addition it is possible to use soft-magnetic coil cores in order to reduce the current demand for production of the alternating magnetic field. In that respect the configuration of the coil cores can be utilised to pass a larger proportion of the magnetic flux under the surface of the body.

Preferably the induction device includes at least one horseshoe-shaped electromagnet. They advantageously produce a spatially delimited magnetic field, the extent of which approximately corresponds to the pole spacing and in turn induces currents which flow predominantly tangentially around the field-filled space. In a simple fashion, that permits comparatively accurate positioning of the device with respect to the treatment region of the vessel.

In a further preferred feature the excitation device has a positioning device for positioning at least one pole of the electromagnet with respect to the body of the patient in order in that way to permit simple and reliable positioning to be effected.

Preferably the device according to the invention with a stimulation device for the direct induction of stimulation currents in the body tissue is used in conjunction with an implant according to the invention for insertion into the vessel in question. That may involve for example a stent. The implant has a tubular body which is intended to bear against the wall of the vessel. The tubular body at least in a portion-wise manner comprises a soft-magnetic material. That in turn provides for concentrating the magnetic field in the tubular body of the implant and in the environment thereof so that a greater electrical field is induced in particular in the space outside the implant in the immediate proximity of the implant surface, than in a vessel without such an implant. That affords an advantageous boost effect for the stimulation currents precisely in the region which is to be stimulated.

In other advantageous variants of the device according to the invention the excitation device serves for contact-less introduction of the stimulation energy which serves to produce the stimulation currents into an implant which is arranged in the region of the vessel, which is to be treated. The implant may involve in particular a stent. Those variants are advantageous especially when such an implant, that is to say for example a stent, is or has to be arranged at the location of the vessel, which is to be treated. Such a stent may be necessary for example to hold the vessel in a dilated position which the vessel cannot assume or can no longer assume of its own accord.

In those cases the stimulation energy is firstly coupled into the implant and then coupled out of same in the appropriate form and delivered directly to the region to be treated. That has the advantage that the action of the stimulation is concentrated precisely on the area around the implant, which is to be the subject of treatment, while other regions of the body are not affected.

The stimulation energy can be coupled into the implant, that is to say for example the stent, in various ways. Thus, preferred variants of the device according to the invention provide that the excitation device includes an induction device for inductive coupling of the stimulation energy into the implant. In other words, suitable magnetic alternating fields cause corresponding currents to be induced in the implant which is of a suitable configuration, and they are in turn used directly or by way of suitable active and/or passive elements of the implant to produce the corresponding stimulation currents. In that case, the magnetic alternating field may already involve a corresponding low frequency and/or low-frequency modulation. Additionally or alternatively a plurality of electrical fields can also be induced in the implant, which are then superimposed to form an electrical alternating field involving correspondingly low-frequency modulation. That can be effected for example by at least two high-frequency electrical alternating fields with a suitably slight frequency difference being produced and superimposed on each other in the manner of a beat.

In other preferred variants of the device according to the invention the excitation device includes a transmitting device for coupling the stimulation energy into the implant in the form of electromagnetic oscillations. In that case the implant includes an antenna element designed in the fashion of an antenna. In other words, by means of electromagnetic oscillations, corresponding currents are produced in the antenna element of the implant, which are in turn used possibly by way of suitable active and/or passive elements of the implant to produce the desired stimulation currents. In that case, the electromagnetic excitation oscillation may already involve suitable low-frequency modulation. Alternatively or additionally it is also possible here again to produce a plurality of electrical currents in the implant, which are then superimposed on each other to form a suitably low-frequency electrical alternating current. That can be effected for example by at least two high-frequency electrical alternating currents with a suitably slight frequency difference being produced and superimposed on each other in the manner of a beat.

The transmission frequency of the transmitting device is preferably so selected that the frequency of the electromagnetic waves received by the antenna element in question corresponds to the resonance frequency of the antenna element as that makes it possible to achieve an optimum energy coupling-in effect. It will be appreciated however that it is also possible to operate with a certain mismatching between the transmission frequency and the resonance frequency of the antenna element. In this respect moreover it is to be noted that the frequency of the electromagnetic waves received by the antenna element is not identical to the transmission frequency (in vacuum) of the transmitting device, by virtue of the change due to the dielectric of the body tissue.

Preferably there is provided a device for focusing the electromagnetic oscillations in the region of the implant in order to reduce the energy flow through tissue which is not in the treatment region in regard to having the minimum possible adverse effect on the tissue which is in the transmission path but which is not to be treated. That device for focusing electromagnetic oscillations can be designed in any known fashion. Preferably it involves an elliptical reflector, at the focal points of which are arranged the transmitting device and the implant.

The invention further concerns an implant for insertion into a vessel in an animal or human body. The vessel may again involve any vessel in the body, preferably it again involves a blood vessel. The implant can be of any desired configuration. It is particularly advantageous however if the implant is a stent as a stent does or can perform still further functions.

The above-specified object is attained with the implant according to the invention in that the implant is adapted to stimulate cells of the vessel in which it is implanted by means of stimulation currents, such stimulation influencing the cell-growth mechanisms. In that respect, stimulation can serve in the above-described manner both to inhibit and also to stimulate the cell-growth mechanisms. As already mentioned, that configuration is particularly advantageous if the implant, for example a stent, already has to be implanted in any case for other reasons in the region of the vessel, which is to be treated. That is the case for example when the stent is required in order to hold the vessel expanded against a return force.

For that purpose the implant can be provided with its own suitably long-life or rechargeable energy supply and a suitable control circuit for controlling the delivery of energy.

In other variants which are preferred because they are of a compact nature and simple to implement the implant is adapted to couple out inductively coupled-in stimulation energy in the form of preferably low-frequency stimulation currents. In that case, alternating currents are induced in the implant by externally generated magnetic alternating fields. For that purpose it is possible to provide for example a magnetic alternating field which involves suitable low-frequency modulation. The induced alternating currents are in turn used directly or by way of suitable active and/or passive elements of the implant to produce the corresponding stimulation currents. If the implant for example involves a stent, those elements can be embedded in a suitable semiconductor coating or semiconductor layer of the stent body which is of a conventional configuration. Equally they can be arranged on the stent on a separate carrier element which is preferably not mechanically loaded or only slightly loaded, upon implantation of the stent.

Additionally or alternatively it is also possible for a plurality of alternating currents to be induced in the implant, which currents are then superimposed to form an electrical alternating current involving suitable low-frequency modulation. That can be effected for example by at least two high-frequency alternating currents with a correspondingly slight frequency difference being produced and superimposed on each other in the manner of a beat.

The implant can be provided with at least one active element which with a capacitive element forms a resonance circuit. To produce stimulation currents involving low-frequency modulation the resonance frequency of the resonance circuit can be in the range of a high-frequency carrier frequency which then entails suitable low-frequency modulation by virtue of suitable modulation of the excitation amplitude. A plurality of such resonance circuits can also be provided for the above-described superimposition of the currents, those resonance circuits then being interconnected with each other for the superimposition procedure. If the implant for example involves a stent those inductive and capacitive elements can be embedded in a suitable coating or layer on the implant. Equally they can be arranged on the stent on a separate carrier element which is preferably mechanically not loaded or only slightly loaded, upon implantation of the stent.

Preferably, the implant according to the invention includes a tubular body which is intended to bear against the wall of the vessel and which to afford a resonance circuit is at least in a portion-wise manner in the form of an induction coil. That means that a relatively large amount of room is available in regard to the configuration of the inductor means, which has a positive effect on the maximum input of energy into the coil by virtue of higher possible numbers of turns and coil and conductor cross-sections. In that respect the implant itself may be in the form of a helix, to form the coil. It is however also possible for the winding to be formed by a coating with suitable conductive turns portions on the tubular body which is then of any desired configuration. It is equally possible for the winding to be formed by suitably conductive portions of the tubular body which is then of any desired configuration.

The ends of the induction coil in question can be interconnected with a capacitive element arranged at any location on the stent, to afford the resonance circuit. It is however also possible to provide in each case only small plates or pads instead of a discrete capacitor at each of the ends of the turns of the coil. The junction capacitances thereof then form together with the electrical connection through the body tissue or the body fluid in the vessel two capacitors which are connected in succession. In order to increase the capacitance the pads can be provided with a fractal surface as is used for example for electrodes of cardiac pacemakers. To increase the dielectric strength the pads can additionally be provided with a thin insulating layer.

Other advantageous variants of the implant according to the invention are distinguished in that the implant is adapted for coupling out stimulation energy which is coupled in by means of high-frequency electromagnetic waves, in the form of stimulation currents involving a low frequency and/or low-frequency modulation, in which case it includes an antenna element designed in the nature of an antenna, for coupling in the stimulation energy.

In that case, an external transmitting device is used for coupling in the stimulation energy in the form of electromagnetic oscillations into the implant which accordingly at least in a portion-wise manner is designed in the manner of an antenna. In other words, currents are produced in the antenna element by means of suitable electromagnetic oscillations. In this case the electromagnetic excitation oscillation can already suitably involve low-frequency modulation. The currents produced in that way are again used directly or by way of suitable active and/or passive elements of the implant to produce the corresponding stimulation currents. If the implant for example involves a stent those active and/or passive elements can be embedded in a suitable semiconductor coating or semiconductor layer of the stent body which is of a conventional configuration. Equally they can be arranged on the stent on a separate carrier element which is preferably mechanically not loaded or only slightly loaded upon implantation of the stent.

Additionally or alternatively a plurality of alternating currents can be produced in the implant by electromagnetic oscillations at different frequencies, which alternating currents are then superimposed to form an electrical alternating current involving suitable low-frequency modulation. That can be effected for example by at least two high-frequency alternating currents with a correspondingly slight frequency difference being produced and superimposed on each other in the manner of a beat.

The implant can be provided with at least one antenna element. To provide for the described superimposition of the currents, it is also possible to provide two such antenna elements which are then interlinked for the superimposition effect.

If the implant for example is a stent those antenna elements can be embedded in a suitable coating or layer on the implant. Equally they can be arranged on the stent on a separate carrier element which is preferably mechanically not loaded or only slightly loaded upon implantation of the stent.

In a configuration which is preferred because it is simple to manufacture the implant includes a tubular body which is intended to bear against the wall of the vessel and which at least in a portion-wise manner is in the nature of a dipole antenna. In that case the entire body can function as an antenna, in which case then a suitably insulating connection between the two halves of the body must be provided at the center. It is however also possible for a conductive layer which is separated from the tubular main body by an insulating layer or a conductive layer arranged on a non-conductive tubular main body to be designed in the manner of a dipole antenna.

In preferred developments of the implant according to the invention there is provided a coupling-out unit which includes a conversion unit for conversion of the coupled-in stimulation energy into stimulation currents which are of low frequency and/or involve low-frequency modulation. The conversion unit may involve the above-described active or passive elements. In that case, the conversion unit preferably includes an electronic circuit for conversion of a high-frequency current into a stimulation current which is of low frequency and/or involves low-frequency modulation. That is further preferably in the form of a coating on the substrate.

The conversion unit however may also simply involve a circuitry arrangement as also described hereinbefore for the superimposition of two alternating currents.

In regard to the frequencies or modulation frequencies of the stimulation currents which are to be coupled out by the implant, it is to be noted that they are in the ranges already described hereinbefore in relation to the device according to the invention.

The present invention further concerns an arrangement comprising a stimulation device according to the invention and an implant in accordance with the invention which is adapted to said stimulation device, as can be used in particular for test or calibration purposes for the stimulation device and additionally or alternatively the implant.

BRIEF DESCRIPTION OF THE DRAWINGS

Further preferred configurations of the present invention will be apparent from the appendant claims and the description hereinafter of preferred variants of the invention with reference to the accompanying drawings in which:

DETAILED DESCRIPTION OF THE INVENTION

Figure 1:
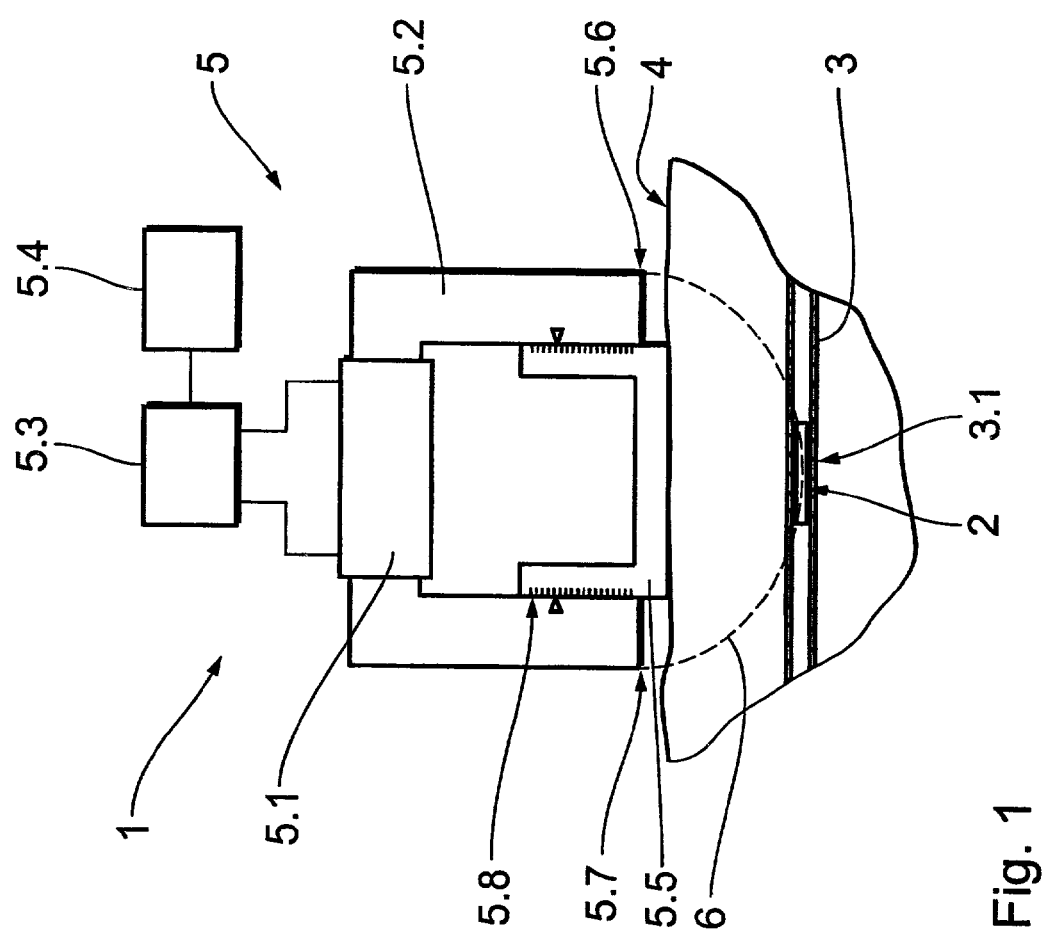
FIG. 1 is a diagrammatic view in section through part of an arrangement comprising a stimulation device according to the invention and an implant according to the invention.

FIG. 1 is a diagrammatic view in section through part of an arrangement comprising a device 1 according to the invention for preventing or slowing down the formation of stenoses and an implant according to the invention in the form of a stent 2 which is arranged in a blood vessel 3 to be treated at a certain depth under the surface 4 of the body of a patient.

The device 1 includes an excitation device 5 which is adapted for the contact-less production of stimulation currents in a region 3.1 of the vessel 3, which is to be treated. For that purpose it includes an electromagnet comprising a coil 5.1 and a horseshoe-shaped core 5.2 together with a supply device 5.3 which is connected to the coil 5.1 and which is controlled by way of a control device 5.4.

The excitation device 5 further includes a positioning device 5.5 which can be applied to the surface 4 of the body of the patient and by way of which the poles 5.6 and 5.7 of the electromagnet can be positioned with respect to the treatment region 3.1. Scales 5.8 are provided to make the positioning operation easier.

In the illustrated example, the excitation device 5 is of such a design configuration that it produces a magnetic field at a carrier frequency of above 1 kHz and with suitable low-frequency modulation, which issues at the poles 5.6 and 5.7 of the electromagnet and which approximately fills a space as is indicated by the contour 6. The diameter of the space indicated by the contour 6 approximately corresponds to the spacing of the two poles 5.6 and 5.7. The poles 5.6 and 5.7 are positioned by way of the positioning device 5.5 in relation to the treatment region 3.1 in such a way that the contour extends in the region of the stent 2.

Figure 2:
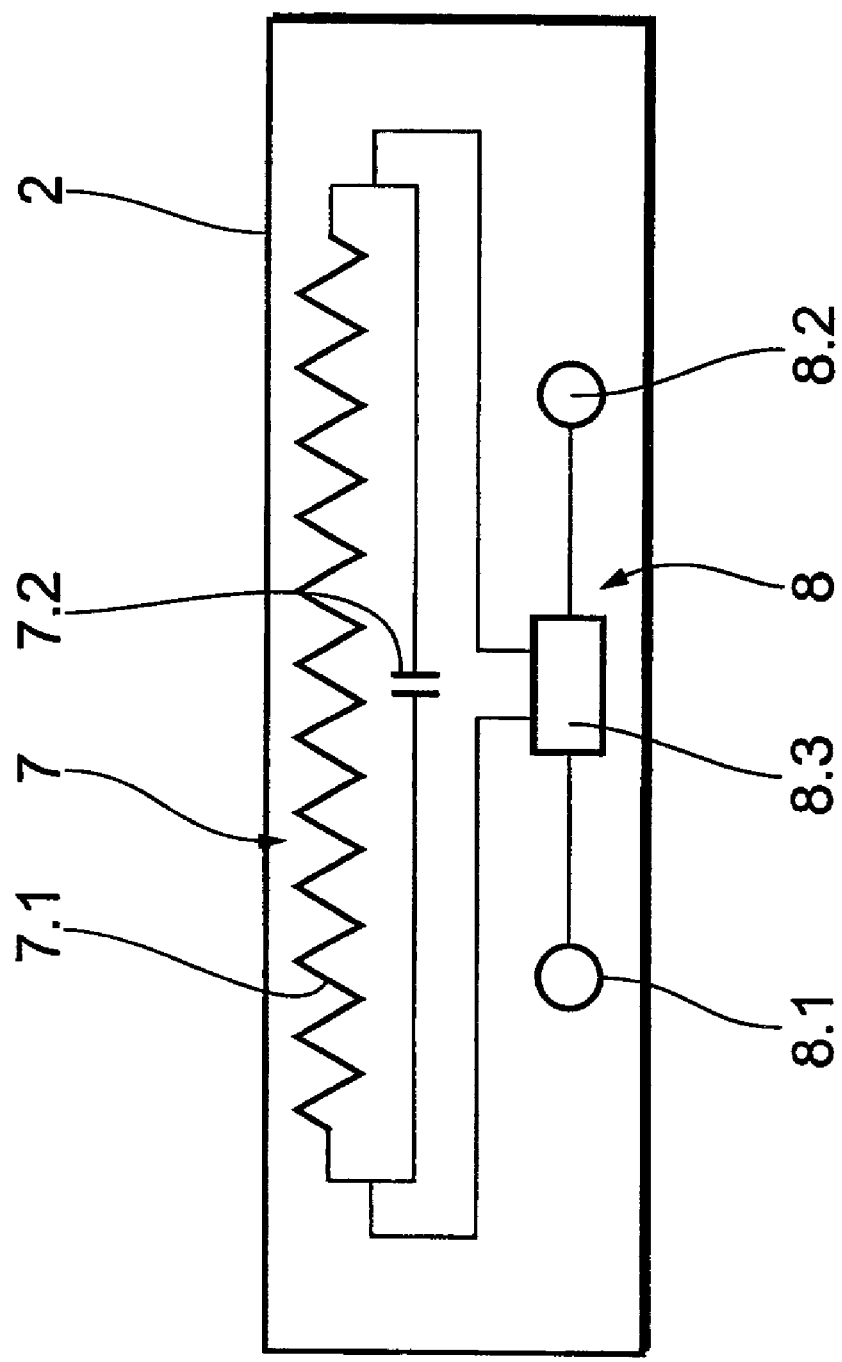
FIG. 2 is a diagrammatic view of a preferred embodiment of the implant from FIG. 1.

The stent 2 is adapted to couple out the stimulation energy which is inductively coupled in by way of the magnetic field and which is delivered by the excitation device 5, in the form of stimulation currents involving low-frequency modulation. For the purposes of coupling in the stimulation energy, as diagrammatically shown in FIG. 2, it is provided with a resonance circuit 7 which comprises an inductive element 7.1 and a capacitive element 7.2 and whose resonance frequency corresponds to the carrier frequency of the magnetic field. The resonance circuit 7 is connected to a coupling-out unit 8. This includes electrodes 8.1 and 8.2 and a conversion unit 8.3 which possibly converts the high-frequency currents induced in the resonance circuit 7 into low-frequency stimulation currents which are then delivered to the blood vessel 3 by way of the electrodes 8.1 and 8.2.

The conversion unit 8.3 includes an electronic circuit which possibly converts the high-frequency currents induced in the resonance circuit into low-frequency stimulation currents. For that purpose the electronic circuit includes per se known passive circuit elements. It will be appreciated however that other variants may also use active circuit elements or a combination of active and passive circuit elements.

The resonance circuit 7 and the coupling-out unit 8 are provided in appropriate coatings on the body of the stent 2. It will be appreciated however that in other variants for example the stent body itself or a portion of the stent body can represent the inductive and/or the capacitive element.

It will further be appreciated that, in other variants of the stent according to the invention, there may be provided a plurality of resonance circuits. They may then be of such a configuration for example that they involve only slightly different resonance frequencies. Those resonance circuits are then only suitably interconnected so that their induced alternating currents are superimposed on each other in the manner of a beat with the appropriate modulation frequency.

The modulation frequency of the stimulation currents is in the range of the frequencies at which distribution of secondary messenger substances controlling cell growth, such as cyclic adenosine monophosphate (cAMP) in the cells of the vessel is influenced. In the illustrated example, only one coupling-out unit is shown. It will be appreciated that other variants may also have a plurality of such coupling-out units as the frequency required to produce the influencing effect can differ from one cell type to another and possibly a plurality of cell types have to be suitably stimulated.

For blood vessels like the blood vessel 3 the frequency or modulation frequency of the stimulation currents is preferably in the range of the frequencies at which distribution of secondary messenger substances controlling cell growth in the smooth muscle cells and additionally or alternatively in the endothelium cells and additionally or alternatively in the fibroblasts of the vessel is stimulated as growths of those cell types involve the main contribution to stenosis formation, in particular in blood vessels.

It will be appreciated that in other variants the distribution of those secondary messenger substances can also be inhibited in order to provide for stimulation of cell growth, as described above. It will likewise be appreciated that the level of concentration of other messenger substances may also have a contrary influence on the cell growth or the cell division activity of the cells and distribution of those messenger substances is accordingly influenced in the corresponding opposite manner.

The intensity of the magnetic field produced by the excitation device 5 in the illustrated example is so selected that the stimulation currents in the tissue to be stimulated reach a current density of at least 5 $\mu A/cm^2$.

The control device 5.4 can control the stimulation with any predeterminable stimulation procedures in respect of time. In particular it has a time control circuit (not shown) which after a given predeterminable stimulation time is adapted to provide for stepwise reduction in the level of stimulation intensity. That permits what is referred to as 'winding-down' of the treatment, in which artificial suppression of cell growth processes is reduced stepwise in order to prevent an overshoot growth of the cells in response to abrupt termination of the treatment. It will be appreciated that, in other variants, it can also be adapted to provide for a continuous reduction in the level of stimulation intensity and additionally or alternatively also to provide for a stepwise or continuous reduction in the frequency of stimulation.

The device illustrated in FIG. 1 can also be used in a modified fashion without a corresponding implant in the blood vessel. In such cases the stimulation current is induced directly in the tissue to be treated, by suitable magnetic fields. In that case, either a magnetic field involving suitable low-frequency modulation is produced by the excitation device or higher-frequency alternating magnetic fields involving slightly different frequencies, which are produced for example by two electromagnets, are superimposed on each other so that the electrical alternating fields induced thereby are superimposed on each other in the manner of a beat to provide a stimulation field of suitably low frequency.

In developments of the last-described variants, it is also possible to use a stent according to the invention which produces concentration of the magnetic field in its environment merely by being at least partially composed of a soft-magnetic material which is possibly enclosed in a biocompatible coating. That provides that the induced stimulation currents are concentrated on the region of the vessel wall, which is in fact just to be treated. In this case the entire stent body can comprise a soft-magnetic material which is then possibly provided with a suitable biocompatible coating. It will be appreciated however that a laminate structure made up of materials with different magnetic properties is also a possible option.

Figure 3:
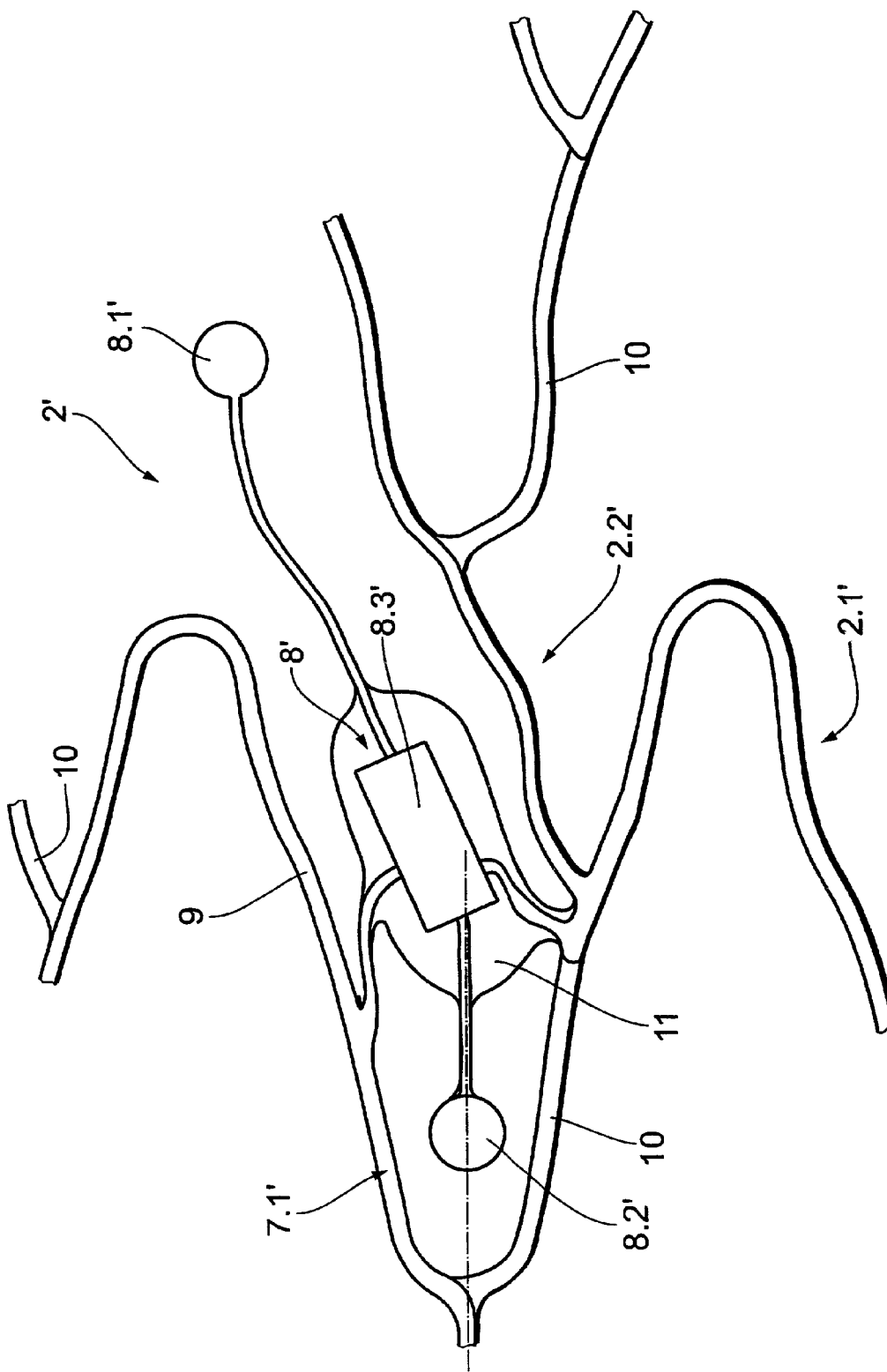
FIG. 3 is a diagrammatic view of a detail of a further preferred embodiment of an implant according to the invention.

FIG. 3 shows a detail of a development of the peripheral surface of a stent 2' according to the invention, which in known manner comprises bar elements 2.1' which extend in a meander configuration in the peripheral direction of the stent 2' and which are connected together in the longitudinal direction of the stent 2' by connecting bars 2.2'. In this case, the stent 2' is designed in the manner described hereinbefore with reference to FIGS. 1 and 2 for inductively coupling in stimulation energy so that here only its particular features will be discussed in detail.

The inductive element 7.1' is formed by a conductive layer 9 on the bar elements 2.1' and the connecting bars 2.2', while to provide a coil non-conductive regions 10 are provided on the bar elements 2.1' and the connecting bars 2.2'. The coupling-out unit 8' is connected to the conductive layer 9, being arranged on a mechanically scarcely loaded pad 11 which comprises the material of the bar elements and is connected thereto. The stimulation electrodes 8.1' and 8.2' are connected to the conversion unit 8.3' of the coupling-out unit 8' and are formed by a conductive layer on suitable extensions of the pad 11.

In this case, the electronic circuit elements of the conversion unit 8.3' are provided in a suitable semiconducting SiC coating on the pad. In this case the material of the bar elements 2.1' and the connecting bars 2.2' can be electrically insulating. It will be appreciated however that in other variants it is also possible simply to provide an insulating layer between the base material and the conductive layer. It will further be appreciated that the entire stent can be provided at least on its side towards the vessel, except for the stimulation electrodes, with an additional insulating coating.

It will be appreciated that a plurality of such coupling-out units with stimulation electrodes can be distributed over the stent in order to achieve stimulation over a large area.

Figure 4:
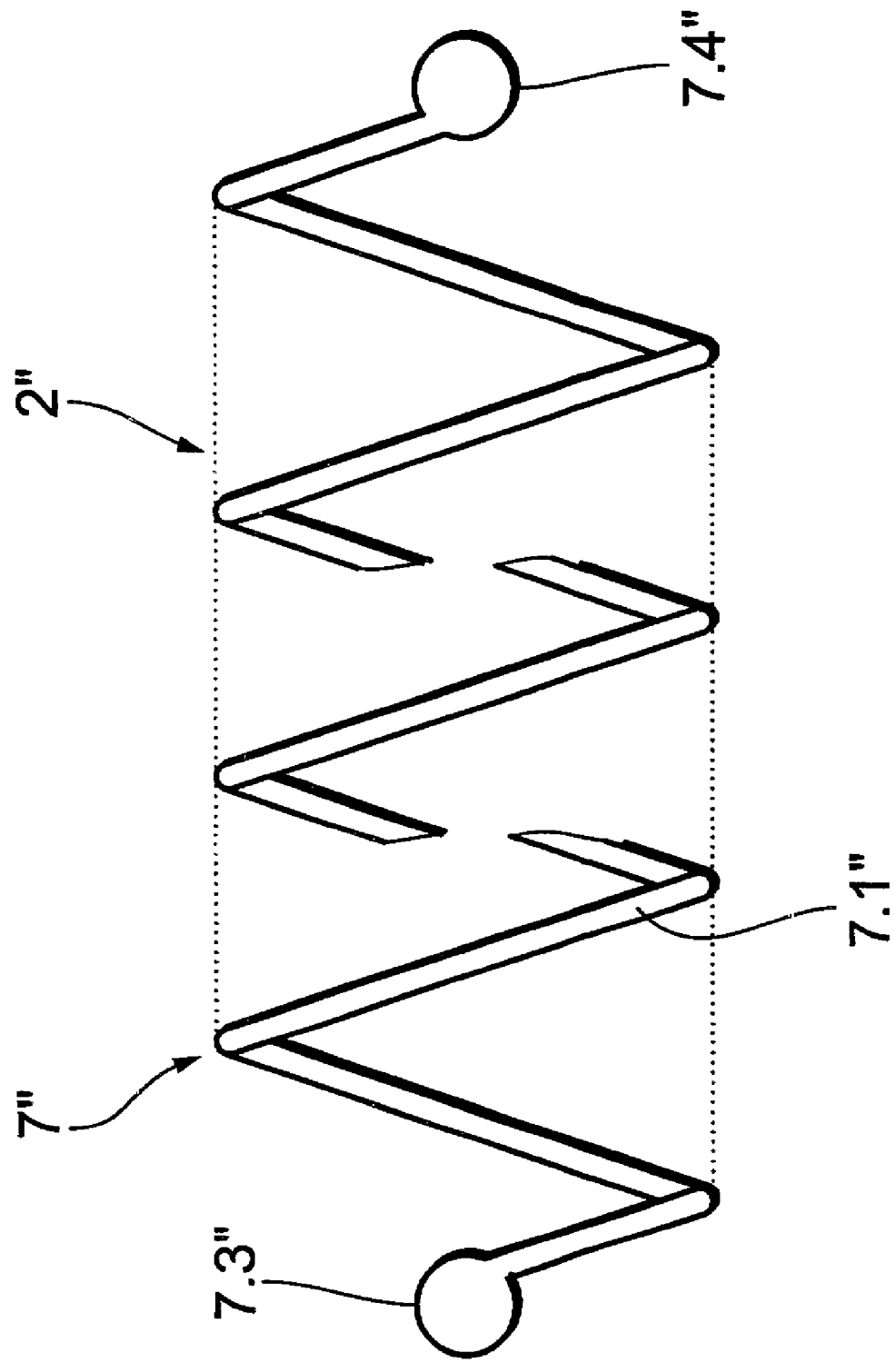
FIG. 4 is a diagrammatic view of a preferred embodiment of an implant according to the invention.

FIG. 4 shows a further preferred embodiment of a stent 2" according to the invention for inductively coupling in the stimulation energy. In its fundamental mode of operation this variant does not differ from the variants described with reference to FIGS. 1 through 3 so that here too only the differences or particularities will be discussed in further detail.

The body of the stent 2" is here formed in the manner of a coil from an electrically conductive material. It thus forms the inductive element 7.1" for the resonance circuit 7". The capacitive element of the resonance circuit 7" is formed by two pads 7.3" and 7.4" at the respective ends of the stent 2". The junction capacitances thereof together with the electrical connection through the body tissue or the body fluid in the vessel form two successively connected capacitors. To increase capacitance, the pads 7.3" and 7.4" are provided with a fractal surface as is used for example for electrodes of cardiac pacemakers.

This variant may also have a coupling-out unit of the design configuration as described hereinbefore. It will be appreciated however that this can also be omitted, with a suitably selected frequency or modulation frequency for the magnetic field, and then the pads also form the stimulation electrodes.

Figure 5:
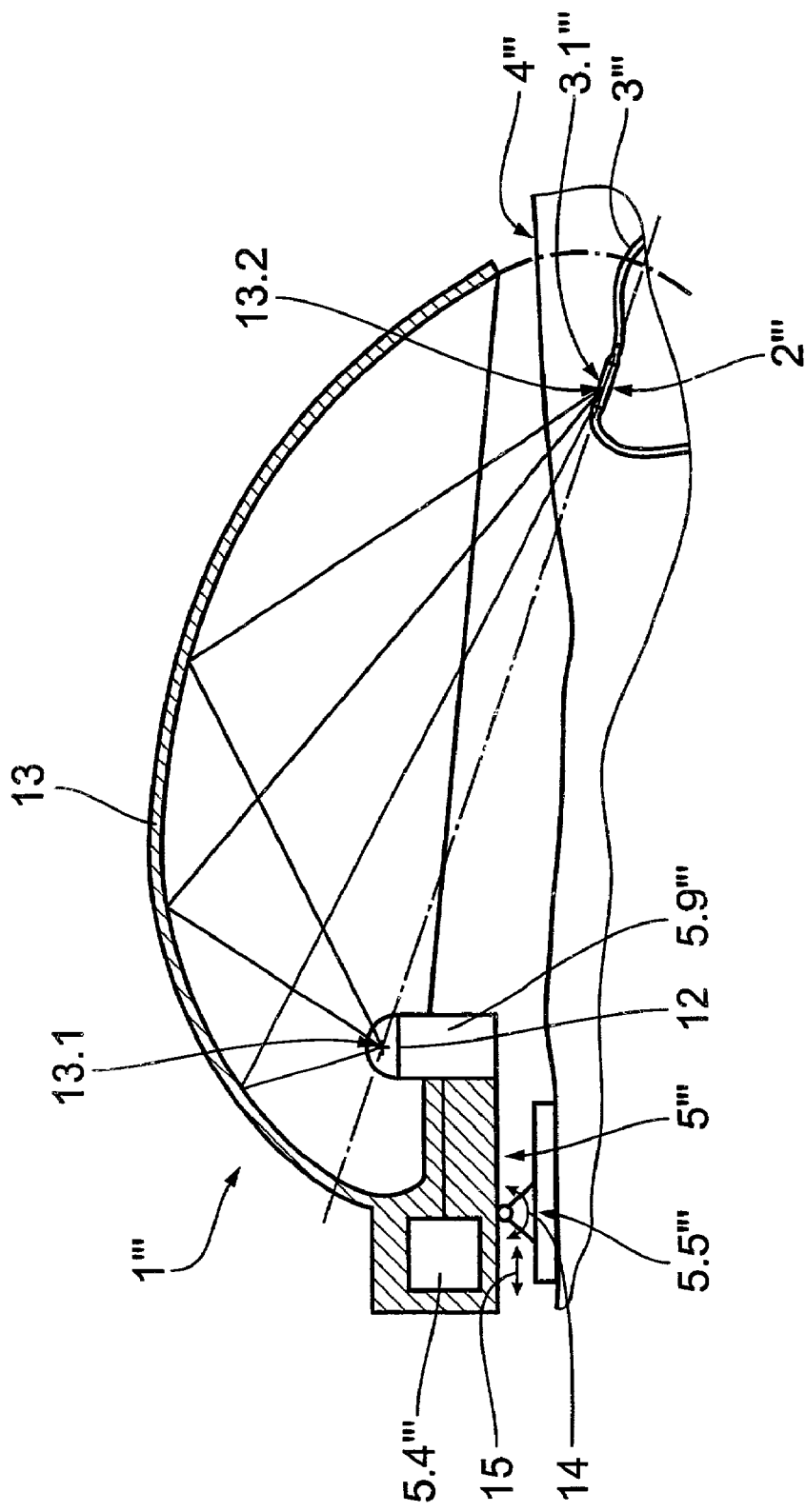
FIG. 5 is a diagrammatic view in section through part of a further arrangement comprising a stimulation device according to the invention and an implant according to the invention.

FIG. 5 shows a diagrammatic view in section through part of an arrangement comprising a device 1''' according to the invention for preventing or slowing down the formation of stenoses and an implant according to the invention in the form of a stent 2''' which is arranged in a blood vessel 3''' to be treated at a certain depth beneath the surface 4''' of the body of a patient. The stent 2''' includes an antenna element which is formed (not shown) in the manner of an antenna and which is adapted to couple in stimulation energy in the form of electromagnetic waves.

The device 1''' has an excitation device 5''' which is adapted for contact-less production of low-frequency stimulation currents in a region 3.1''' to be treated in the vessel 3'. For that purpose it includes a transmitter 5.9''' which can emit electromagnetic waves into the half-space above the contour 12, a control device 5.4''' connected to the transmitter 5.9''' and a reflector 13 associated with the transmitter 5.9'''. That reflector 13 is formed by a portion of an ellipsoid of revolution, with the transmitter 5.9''' being arranged at the first focal point 13.1 of that ellipsoid of revolution. The excitation device 5''' is so arranged that the stent 2''' is arranged at the second focal point 13.2 of the ellipsoid of revolution. That causes the electromagnetic waves of the transmitter 5.9''' to be focussed at the location of the stent 2'''.

It will be appreciated that in other variants the reflector may be of a shape which differs from an ellipsoid of revolution. That is preferably so selected that the defocusing effect caused by the different wavelengths in air and body is compensated.

The excitation device 5''' further includes a positioning device 5.5''' which can be applied to the surface 4''' of the body of the patient. The position of the second focal point 13.2 of the reflector can be varied by way of the positioning device 5.5''', for adaptation to different positions of the stent 2''' or the treatment region 3.1''', by pivotal movement in the direction of the arrow 14 or displacement in the direction of the arrow 15. In addition mutual polarisation can be oriented in the optimum fashion, from transmitter to receiver, by rotation of the transmitter 5.9''' in the plane of the contour 12.

In the illustrated example the excitation device 5''' is of such a nature that it delivers stimulation energy in the form of high-frequency electromagnetic waves which are focussed on to the stent 2''' and coupled thereinto. The stent 2''' in turn is adapted to couple out the coupled-in energy delivered by the excitation device 5''', in the form of low-frequency stimulation currents.

Figure 6:
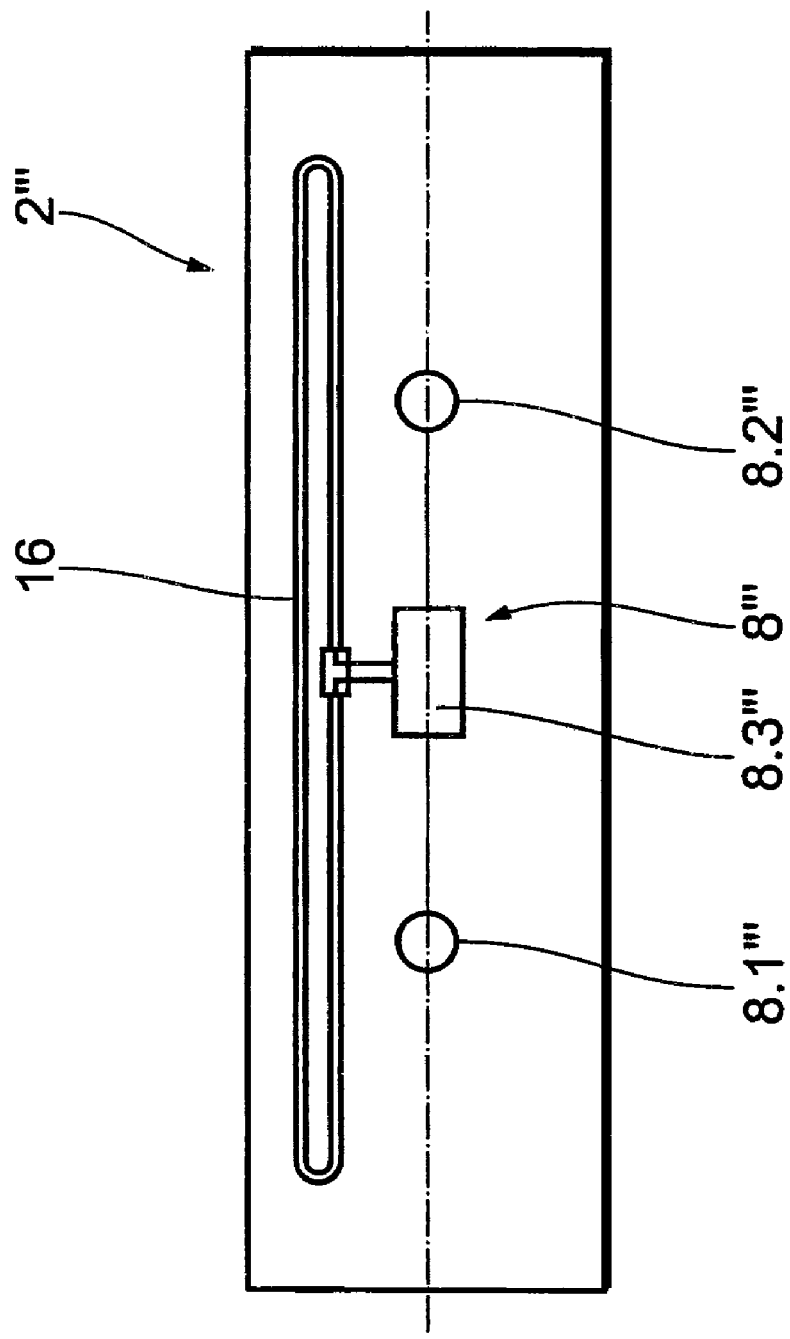
FIG. 6 is a diagrammatic view of a preferred embodiment of the implant from FIG. 5.

As can be diagrammatically seen from FIG. 6, the stent 2''' is provided with a folded dipole 16 for coupling in the stimulation energy. The length thereof corresponds to a quarter of the wavelength of the electromagnetic waves which are produced by the transmitter 5''' and which are incident at the folded dipole 16. In this case the frequency received by the folded dipole 16, due to the change caused by the dielectric of the body tissue, does not correspond to the transmission frequency (in vacuum) of the transmitter 5'''. The folded dipole 16 is connected to a coupling-out unit 8''' which converts the high-frequency currents produced in the folded dipole 16 into low-frequency stimulation currents which are then delivered to the blood vessel 3''' by way of the electrodes 8.1''' and 8.2'''.

The conversion unit 8.3''' of the coupling-out unit 8''' includes an electronic circuit which converts the high-frequency currents produced in the folded dipole 8''' into low-frequency stimulation currents. For that purpose the electronic circuit includes suitable per se known passive circuit elements. It will be appreciated however that other variants can also use active circuit elements or a combination of active and passive circuit elements.

The folded dipole 16 and the coupling-out unit 8''' are provided in suitable coatings or layers on the main body of the stent 2'''. Thus the folded dipole 16 comprises a suitably shaped conductive coating on the main body of the stent 2'''. In this case the main body of the stent 2''' also comprises an electrically conductive material, but the folded dipole 16 is separated therefrom by an insulating intermediate layer. In other variants, the main body of the stent itself may already comprise a suitably insulating material. It will be appreciated moreover that in other variants for example the stent body itself or a portion of the stent body may represent the dipole.

It will further be appreciated that a plurality of dipoles can also be provided in other variants of the stent according to the invention. Then, they can be of such a nature for example that they involve only slightly different resonant frequencies. Those dipoles are then only suitably interlinked so that the alternating currents produced therein are superimposed in the manner of a beat to form a stimulation current of the desired stimulation frequency. It will again be appreciated in this respect that in that case also the transmitter must be suitably designed to emit electromagnetic waves at two frequencies which are suitable for that purpose.

It will further be appreciated that, in other variants, the excitation device can be so designed that it delivers stimulation energy in the form of high-frequency electromagnetic waves which involve low-frequency modulation and which are focussed on to and coupled into the stent. The stent in turn is then adapted to couple out the coupled-in stimulation energy delivered by the excitation device, in the form of suitably modulated low-frequency stimulation currents.

The frequency and/or the modulation frequency of the stimulation currents is in the range of the frequencies at which distribution of secondary messenger substances controlling cell growth, such as cyclic adenosine monophosphate (cAMP) in the cells of the vessel is influenced. In the illustrated example, only one coupling-out unit is shown. It will be appreciated that other variants may also have a plurality of such coupling-out units as the frequency required for the influencing effect can differ from one cell type to another and possibly a plurality of cell types have to be correspondingly stimulated.

For blood vessels such as the blood vessel 3''' the frequency or modulation frequency of the stimulation currents for preventing or slowing down stenosis formation is preferably in the range of frequencies at which distribution of secondary messenger substances for controlling cell growth in the smooth muscle cells and additionally or alternatively in the endothelium cells and additionally or alternatively in the fibroblasts of the vessel is influenced as growths of those cell types involve the main contribution to stenosis formation, in particular in blood vessels. Depending on the respective messenger substance involved, excitation of the distribution thereof can be required, as is the case for example with cyclic adenosine monophosphate (cAMP), but inhibition of the distribution thereof may also be required.

In the illustrated example the intensity of the electromagnetic waves generated by the excitation device 5''' is so selected that the stimulation currents in the tissue to be stimulated reach a current density of at least 5 $\mu A/cm^2$.

The control device 5.4''' can control the stimulation effect with any predeterminable stimulation procedures in respect of time. It has in particular a time control circuit (not shown) which is adapted to provide for a stepwise reduction in the level of stimulation intensity after a given predeterminable stimulation period. That permits what is referred to as 'winding down' the treatment, with the artificial suppression of cell growth processes being reduced stepwise in order to prevent overshooting growth of the cells in response to abrupt termination of the treatment. It will be appreciated that in other variants it may also be adapted to provide for a continuous reduction in the level of stimulation intensity and additionally or alternatively also to provide for a stepwise or continuous reduction in the frequency of stimulation.

Figure 7:
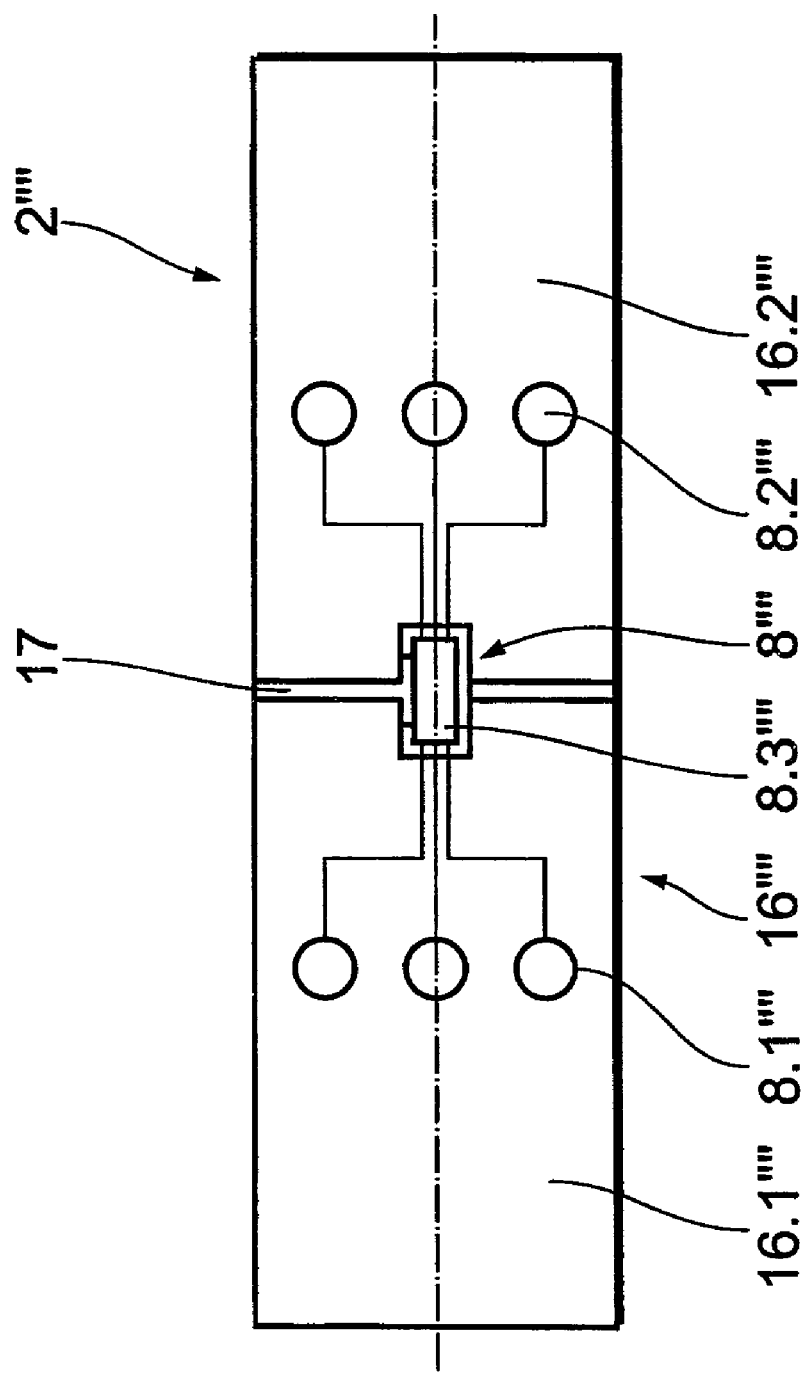
FIG. 7 is a diagrammatic view of a further preferred embodiment of an implant according to the invention.

FIG. 7 shows a diagrammatic view of a further embodiment of a stent 2'''' according to the invention. In this case, the stent 2'''' is adapted to couple in stimulation energy, in the manner described hereinbefore with reference to FIGS. 5 and 6, so that here only its particularities will be discussed in detail.

In this embodiment the dipole 16'''' is in the form of a simple dipole. Its length corresponds to half the wavelength of the electromagnetic waves which are produced by a suitable transmitter and which are incident at the dipole. In this case the frequency received by the dipole 16'''', by virtue of the change caused by the dielectric of the body tissue, is not the same as the transmission frequency (in vacuum) of the transmitter in question. The dipole 16'''' comprises two electrically conductive coatings 16.1'''' and 16.2'''' on the main body of the stent 2'''', which each extend approximately over half the length of the stent 2'''' and which are separated from each other at the center of the stent 2'''' by an insulating layer 17.

The halves 16.1'''' and 16.2'''' of the dipole 16'''' are connected to a coupling-out unit 8'''' at the center of the stent 2'''', which converts the high-frequency currents produced in the dipole 16'''' into low-frequency stimulation currents which then in turn are delivered to the blood vessel in question by way of a row of electrodes 8.1'''' and 8.2'''' which are insulated in relation to the coatings 16.1'''' and 16.2''''. The electrodes 8.1'''' and 8.2'''' can be uniformly distributed over the stent in order to achieve uniform stimulation of the tissue.

The configuration described with reference to FIG. 7 can be embodied with main bodies of any desired configuration for the stent 2''''. Thus, possibly except for the small region in which the conversion unit 8.3'''' is arranged, the stent can be of a known structure of any desired configuration, for example a known mesh structure. The conversion unit can again be arranged on a separate pad, as was described hereinbefore with reference to FIG. 3.

It will be appreciated that in other variants of the implant according to the invention, for example a stent, the main body itself may also form the dipole. In that case, it then comprises two electrically conductive halves which are separated by a non-conductive portion.

What is claimed is:

1. A device for influencing cell-growth mechanisms in vessels, in particular blood vessels, of a human or animal body, comprising:
   an excitation device for producing stimulation energy; and
   an implant, wherein the implant is adapted to be placed in a blood vessel and is further adapted to contactlessly receive stimulation energy from the excitation device and produce stimulation currents in a region to be treated of the vessel, wherein the stimulation currents have a frequency and/or a modulation frequency in the range of frequencies at which distribution of secondary messenger substances controlling cell growth in the cells of the vessel is influenced and wherein the implant is a stent.

2. The device of claim 1, wherein the frequency and/or the modulation frequency of the stimulation currents is in the range of frequencies at which the distribution of cyclic adenosine monophosphate (cAMP) in the cells of the vessel is inhibited or stimulated.

3. The device of claim 2, wherein
   the excitation device produces stimulation currents having frequency and/or modulation frequency in the range of frequencies at which distribution of secondary messenger substances producing cell growth in the smooth muscle cells and/or the endothelium cells and/or the fibroblasts of a vessel is inhibited or stimulated.

4. The device of claim 1, wherein:
   the stimulation currents have frequency and/or modulation frequency in the range of frequencies at which distribution of secondary messenger substances producing cell growth in the smooth muscle cells and/or the endothelium cells and/or the fibroblasts of a vessel is inhibited or stimulated.

5. The device of claim 4, wherein
   the frequency and/or the modulation frequency of the stimulation currents is in the range of frequencies at which the distribution of cyclic adenosine monophosphate (cAMP) in the cells of the vessel is inhibited or stimulated.

6. The device of claim 5, wherein
   the excitation device produces stimulation currents having frequency and/or modulation frequency in the range of frequencies at which distribution of secondary messenger substances producing cell growth in the smooth muscle cells and/or the endothelium cells and/or the fibroblasts of a vessel is inhibited or stimulated.

7. The device of claim 6, wherein
   the stimulation currents in the region to be treated of the vessel have a frequency and/or a modulation frequency of up to 200 Hz.

8. The device of claim 7, wherein
   the stimulation currents in the region to be treated of the vessel have a frequency and/or a modulation frequency in the range of from 10 to 100 Hz.

9. The device of claim 8, wherein the excitation device comprises a time control device for producing a reduction in the level of stimulation intensity and/or the frequency of stimulation.

10. The device of claim 9, wherein the reduction is stepwise.

11. The device of claim 9, wherein the reduction is continuous.

12. The device of claim 1, wherein
    the stimulation currents in the region to be treated of the vessel have a frequency and/or a modulation frequency of up to 200 Hz.

13. The device of claim 12, wherein
    the stimulation currents in the region to be treated of the vessel have a frequency and/or a modulation frequency in the range of from 10 to 100 Hz.

14. The device of claim 1, wherein the excitation device comprises a time control device for producing a reduction in the level of stimulation intensity and/or the frequency of stimulation.

15. The device of claim 14, wherein the reduction is stepwise.

16. The device of claim 14, wherein the reduction is continuous.

17. The device of claim 1, wherein the excitation device comprises an induction device for producing at least one local magnetic alternating field in the treatment region of the vessel.

18. The device of claim 17, wherein the induction device comprises at least one horseshoe-shaped electromagnet.

19. The device of claim 18, wherein the excitation device further comprises a positioning device for positioning at least one pole of the electromagnet with respect to the body.

20. The device of claim 1, wherein the excitation device comprises an induction device for inductively coupling the stimulation energy into the implant.

21. The device of claim 1, wherein the excitation device comprises a transmitter device for coupling the stimulation energy in the form of electromagnetic oscillations into the implant, the implant comprising an antenna element.

22. The device of claim 21, further comprising a device for focusing the electromagnetic oscillations in the region of the implant.

* * * * *